US00PP32467P2

(12) United States Plant Patent
Felker

(10) Patent No.: US PP32,467 P2
(45) Date of Patent: Nov. 17, 2020

(54) ***PROSOPIS* TREE NAMED 'MOJAVE'**

(50) Latin Name: ***P. alba* x *P. glandulosa* var *glandulosa* hybrid**
Varietal Denomination: Mojave

(71) Applicant: Peter Felker, Salinas, CA (US)

(72) Inventor: Peter Felker, Salinas, CA (US)

(73) Assignee: Peter Felker, Salinas, CA (US)

( * ) Notice: Subject to any disclaimer, the term of this patent is extended or adjusted under 35 U.S.C. 154(b) by 0 days.

(21) Appl. No.: 16/501,518

(22) Filed: Apr. 22, 2019

(51) Int. Cl.
*A01H 5/00* (2018.01)
*A01H 6/54* (2018.01)

(52) U.S. Cl.
USPC ..... Plt./216
CPC ..... *A01H 6/54* (2018.05)

(58) Field of Classification Search
USPC ..... Plt./216
See application file for complete search history.

*Primary Examiner* — Susan McCormick Ewoldt
*Assistant Examiner* — Karen M Redden

(57) ABSTRACT

A new and distinct combination of the genes of South American *Prosopis alba* and North American *Prosopis glandulosa* var *glandulosa* for cold hardiness, and erect growth to produce erect, thornless, fast growing ornamental and lumber trees that provide greater adaptability to a much broader range of arid ecosystems than previous *Prosopis alba* ornamental selections.

6 Drawing Sheets

CROSS-REFERENCE TO RELATED APPLICATIONS

This application has a copending application No. 16/501,517 cultivar 'Sonoran' which is a full sibling of previously patented clones as described below.

Latin name of the genus and species of the plant claimed: *P. alba* x *P. glandulosa* var *glandulosa* hybrid.

Variety denomination: 'Mojave'.

BACKGROUND OF THE INVENTION

Field of the Invention

As exemplified by extensive native distribution on the floor of Death Valley, Calif. that is the hottest place on earth, the nitrogen fixing genus *Prosopis* has exceptional heat drought tolerance. *Prosopis* lumber has very low shrinkage and almost equal radial and tangential shrinkage leading to widespread use for fine furniture, flooring and architectural components in southwestern United States, Mexico and Argentina. Its exceptional heat/drought tolerance and broad canopy have led to widespread use as an ornamental tree, particularly in arid California and Arizona. Lack of tolerance to extended periods of 10° F. have limited the use of the most widespread ornamental species with lack of thorns i.e. *P. alba* in southwestern USA. The presence of thorns on cold hardy native species *P. glandulosa* and *P. velutina* and their lack of erect growth have limited their use for ornamentals. Water shortages and water rationing for landscaping in southwestern USA make ornamental trees with low water requirements especially desirable.

In Argentina more than 100,000 tons of logs per year were harvested in the early 2000's for flooring and furniture manufacture but this industry has greatly decreased due to overharvest of native trees. In Texas *Prosopis* lumber harvested from non-cultivated trees is the basis for a substantial cottage industry. Lack of thornless native *Prosopis* with erect growth, and lack of hardiness to approximate 5° F. temperatures of the thornless South America *P. alba* has resulted in lack of plantations necessary to be a commercial lumber tree in the USA. I have used classical breeding techniques to obtain the best combinations of cold hardiness, erect growth and lack of spines from elite North and South American *Prosopis* species.

Specifically, I have crossed a previously described cold hardy spineless *Prosopis alba* with a cold hardy spineless and very erect *Prosopis glandulosa* var *glandulosa* and selected progeny that are spineless, cold hardy, fast growing and very erect for use both as ornamentals and lumber producing trees.

Description of Relevant Prior Art

In this patent, the species descriptions of Burkart (1976 A monograph of genus *Prosopis* (*Leguminosae*). Journal of Arnold Arboretum; 450-525.) has been followed. The parents of the claimed plant described here are the patented U.S. Plant Pat. No. 9,256 thornless *Prosopis glandulosa* var *glandulosa* 'Beth' that has exceptionally erect growth with narrow branch angles and the patented U.S. Plant Pat. No. 9,072 thornless *P. alba*'Laurie' that survived 20 consecutive hours below 20° F. with a minimum of 10° F.

Other patented *Prosopis* clones for use as ornamentals are 'American Mesquite' (U.S. Plant Pat. No. 24,702) that resulted from a seedling of unknown parents, with unknown cold tolerance in an Arizona nursery, "Leslie Roy' (U.S. Plant Pat. No. 23,360) that originated from a cross between an unnamed *P. velutina* and an unnamed *P. chilensis* and is stated to be cold hardy to USDA Zone 7b as it withstood a temperature of minus 12° C. (10 ° F.) and 'Cooper' (U.S. Plant Pat. No. 15,303) that was stated to be *P. alba* but according to Burkart (1976), due to its leaflet spacing was a *P. chilensis*. In Argentina where the author lived for 5 years, temperatures briefly reach 12° F. but little damage results to the *P. alba* due to the less than a one hour early morning duration of the freeze. In contrast the 'Laurie' *P. alba* parent survived 20 consecutive hours below 20° F. with a minimum of 10° F. and 10 years without damage in Austin, Tex. which is USDA cold hardiness zone 8B.

In 2011 hand crosses were made between 'Laurie' and 'Beth' in a greenhouse in Salinas, Calif. using the 'Laurie' as the pollen donor and the 'Beth' as the female parent. The seeds were planted in the same greenhouse on Dec. 4, 2011. On June 2014, progeny of these crosses were successfully asexually propagated by wedge grafting with greater than 80 success. After the cloned progeny were evaluated for erect and spineless habit over a 5 year period in a greenhouse in Salinas Calif., and field plantings in Vista, Calif., the copending 'Sonoran' and 'Mojave' application were discovered and selected for patenting.

The foliage pattern and branch angle has remained constant through more than 2000 wedge grafts through succeeding asexual propagation over an 8-year period onto *P. alba* x *P. glandulosa* rootstock, as well as *P. alba* rootstock in agreenhouse in Salinas, Calif., and in Vista, Calif.

While 'Sonoran' and 'Mojave' were not tested for freeze hardiness, as the most frost susceptible parent, the *P. alba* 'Laurie' is cold hardy to USDA zone 8B and the 'Beth' Texas native parent *P. glandulosa* var *glandulosa* is cold hardy to all of Texas (USDA zones 7A and 6b) it is reasonable to assume that the progeny will possess cold hardiness similar to the most frost susceptible parent i.e. zone 8B.

SUMMARY OF THE INVENTION

For the first time the ornamental tree characteristics of an elite clone of the North American species i.e. thornlessness, cold hardiness to 0° F. and a special erect habit, have been combined with characteristics of an elite South American *Prosopis* i.e. fast growth, thornlessness and more tropical looking foliage (more pinnae and more closely spaced leaflets) to provide a better suite of characteristics than either of the parents, or other *Prosopis* clones being used for ornamentals.

DETAILED BOTANICAL DESCRIPTION OF THE PLANT

All color designations herein are made in accordance with The Royal Horticultural Society Colour Chart Third Edition. This plant is a progeny of hand crosses between *Prosopis alba* (native to Argentina) variety 'Laurie' as the pollen parent and *Prosopis glandulosa* var *glandulosa* (native to south Texas) 'Beth' as the female parent and thus is an interspecific hybrid. Unlike the *P. alba* parent with 4 pair of pinnae and with 52 pairs of leaflets per pinnae or the *P. glandulosa* parent with one pair of pinnae with 10 leaflets per pinnae, 'Mojave' has 2 pairs of pinnae with about 32 pairs of leaflets per pinnae, each about 2.4 mm wide, 11 mm long and with a 1.55 mm spacing between leaflets on the pinnae. The venation of the leaflets is not distinguishable. The 11 cm pinnae length of this new clone was similar to both the *P. alba* parent with 11-13 cm length or the *P. glandulosa* parent with a pinnae length of 12-13 cm. The color of the leaves is Green Group 134B.Upon first frost, the mature leaves fall off and no color change is seen. Nectaries are not visible.

Figure 1:
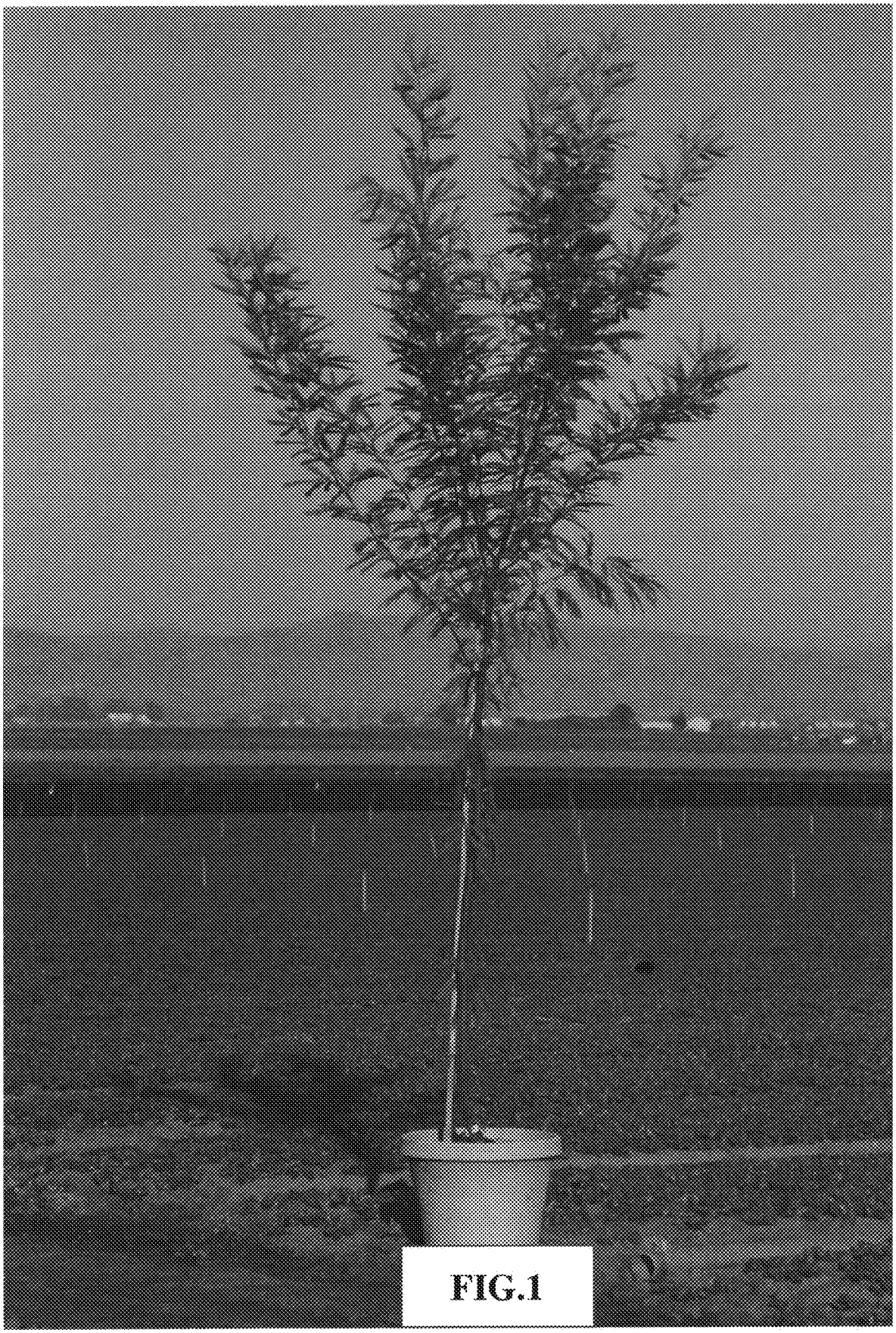
FIG. 1 of a 20 month old 'Mojave' clone illustrates both the very rapid growth and the upright erect branching habit with a crotch angle as low as 6 degrees. It is evident that the *P. glandulosa* parent is contributing the genetic codes to obtain this very narrow branch angle which will be very useful in providing straight trunks for fine lumber production and in avoiding nearly horizontal branches which are more prone to break in windstorms.
Figure 2:
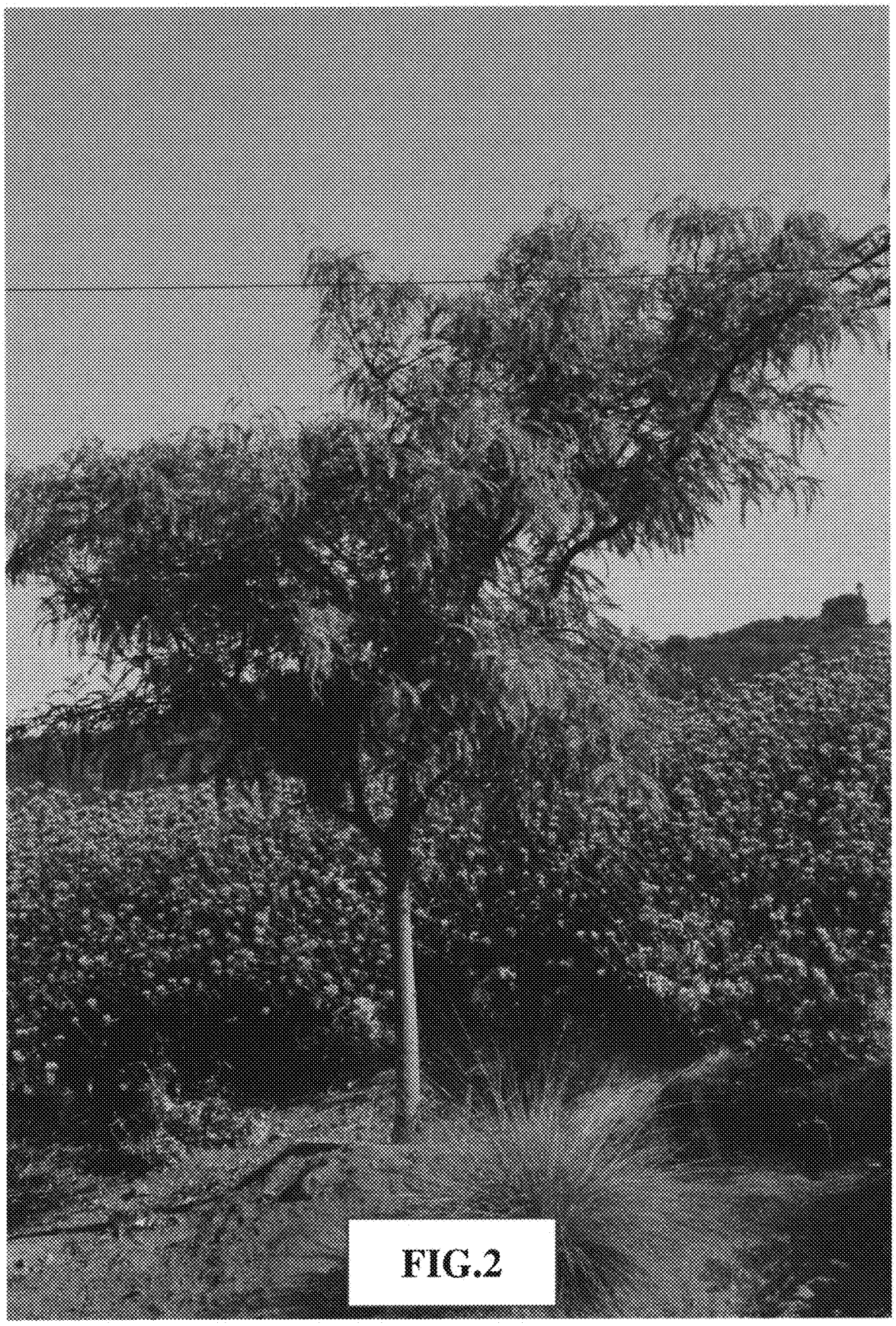
FIG. 2 is a 4-year-old tree that illustrates the erect trunk and the narrow branch angle of the branches.
Figure 3:
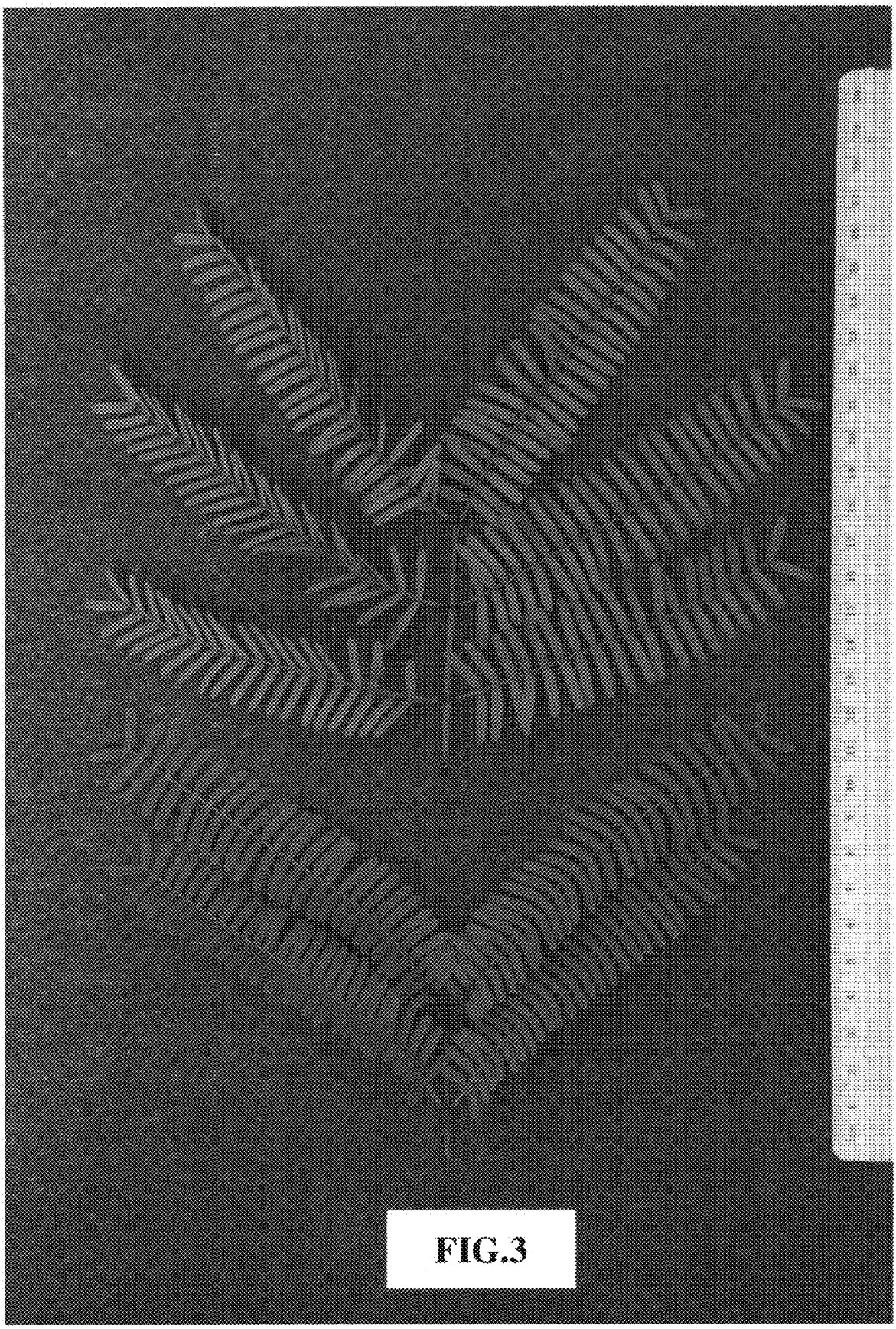
FIG. 3 illustrates the range in leaf morphology of 'Mojave'.
Figure 4:
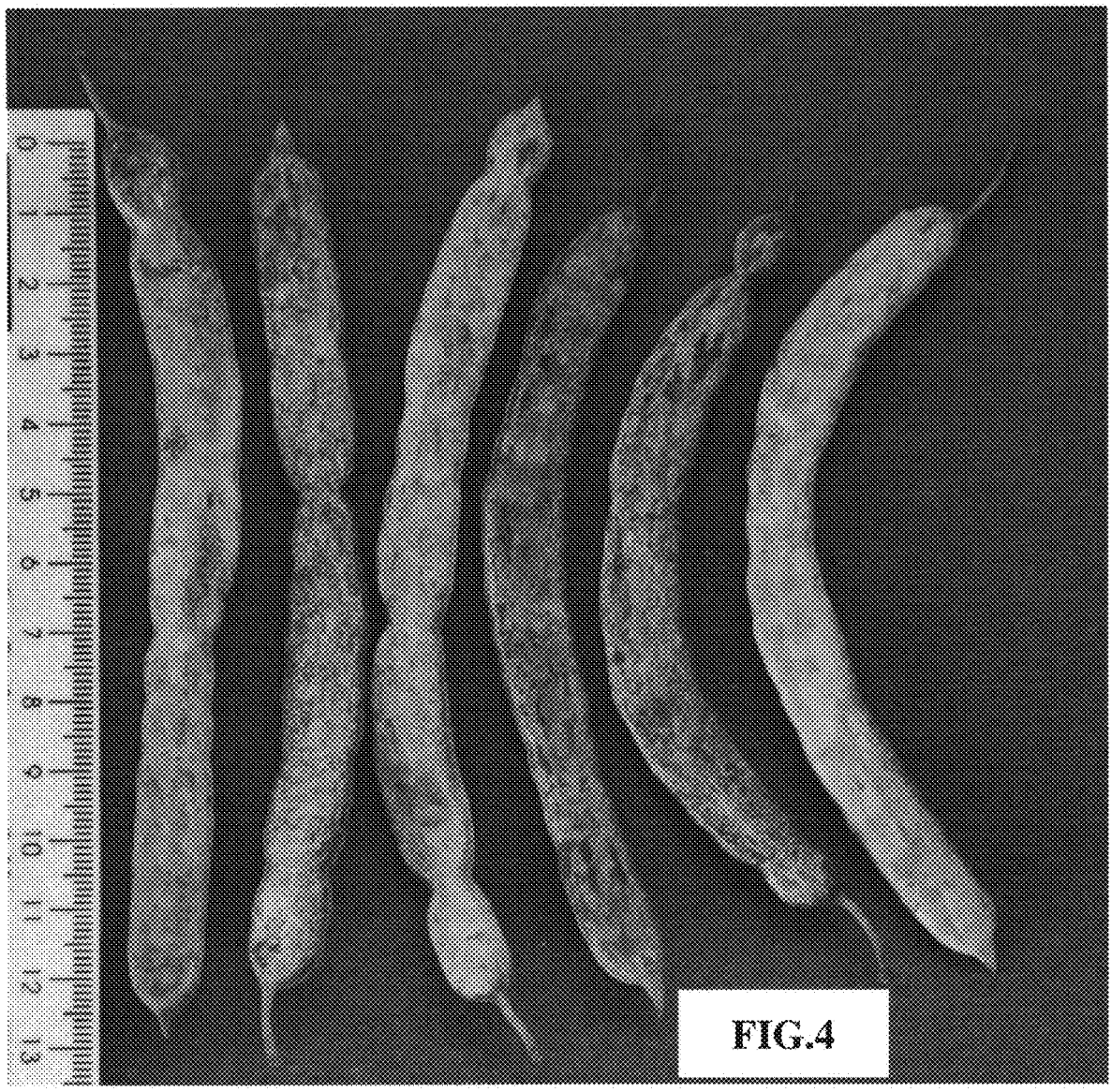
FIG. 4 illustrates the pods of 'Mojave'.

The pods are intermediate in color and form between the patented *P. glandulosa* var *glandulosa* parent (see FIG. 4 of 'Beth') and the *P. alba* parent (sheet 2 of 4 of U.S. Plant Pat. No. 09,072). The pods of the 'Mojave' are 12.5+/−0.43 mm wide and were slightly smaller than the *P. alba* parent 14-16 mm width but wider than the *P. glandulosa* parent i.e. 9 mm. The pods were similar in thickness of 4.7+/−0.17 mm to both the *P. glandulosa* var *glandulosa* parent with 5 mm thickness and the *P. alba* parent with 4-6 mm thickness. The 'Mojave' pods had a mean length of 11.7+/−1.10 cm which is shorter than the 17-20 cm for the *P. glandulosa* parent but similar to the 8-11 cm length for the *P. alba* parent. Some of the 'Mojave' pods were slightly curved unlike the perfectly straight *P. glandulosa* parent and also unlike the very strongly curved pods of the *P. alba* parent. The 'Mojave' pods had reddish (greyed-purple group 187 B & C) streaks similar to the *P. glandulosa* parent and completely different than the yellow tan pods (with no reddish coloration) of the *P. alba* parent.

The number of pods per inflorescence can range from zero to 10 depending on the pollination. Since *Prosopis* is 100% self-incompatible, if no other *Prosopis* is close, or no bees are present, no pods will be produced. Similarly, if many trees of the same 'Mojave' clone are used in large plantings, no pods will result. No pod production from extensive plantings could be desirable in an urban landscape project where the pods must be removed, but not desirable where abundant wildlife is the objective.

The seeds per pod is variable as the longer the pod the more seeds there are. The seeds have a greyed-orange 165 A color, are oval shaped, and are approximately 4.5 mm wide and 7.0 mm long.

The branching angle, sometimes also known as the "crotch angle" is very important in lumber trees as well as ornamental trees. The *P. alba* parent had a weeping, pendulant branching habit with no central stem above 2 m and had several co-dominant main branches with crotch angles of about 60-80 degrees i.e. only slightly above horizontal. In contrast the angle subtended by the main branches from the central trunk in the very unique *P. glandulosa* clone was about 20-25 degrees and therefore was much more vertical than the *P. alba* parent.

Flowering Habits

Figure 5:
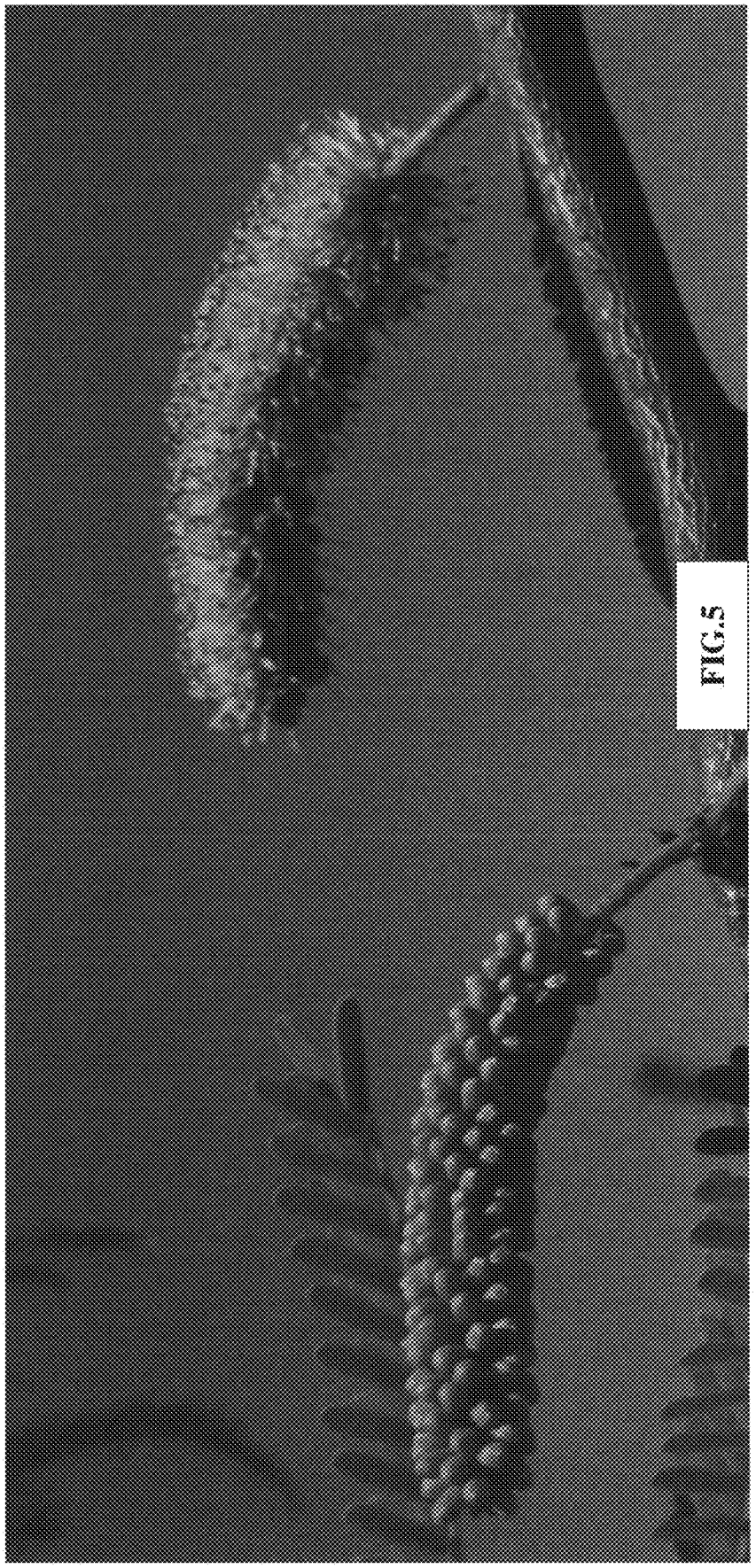
FIG. 5 illustrates the color and morphology of the flowers.

The range in color and shape of an unopened and opened inflorescences are shown in FIG. 5. On the unopened inflorescence, to the left, can be seen hundreds of individual perfect, self-incompatible flowers flower buds each with 10 stamens that have not opened. The inflorescence is approximately 5 cm long and 1.5 cm in diameter. On the right is an opened inflorescence with an overall yellow green 150A color with the small protruding anthers with a yellow group 5 A color. The flowers do not have an odor. Flowers are minute and too small for accurate measurements.

Distinguishing Characteristics of Copending Applications of Full Siblings

As can be seen in the table below, 'Mojave' can be distinguished from the 'Sonoran' clone of the copending application by lack of spines and by average distance between leaflets on the pinnae. In addition, the girth of 'Mojave' is about 4 mm greater than 'Sonoran' for a 2-meter-tall tree of the same height.

TABLE 1

Comparison between 'Mojave' and 'Sonoran'

| Clone | Average of leaflet length (mm) | Average # of leaflets per pinnae | Average of Distance between leaflets (mm) | Average of # pairs of pinnae |
|---|---|---|---|---|
| 'Mojave' | 11.1 | 30.8 | 1.6 | 2.0 |
| 'Sonoran' | 12.4 | 30.2 | 2.2 | 2.0 |

| Clone | Average of pinnae length (mm) | Average of Leaflet width (mm) | Spine length (mm) |
|---|---|---|---|
| 'Mojave' | 11.0 | 2.4 | 0.0 |
| 'Sonoran' | 11.6 | 2.6 | 5.0 |

General Tree Characteristics

Figure 6:
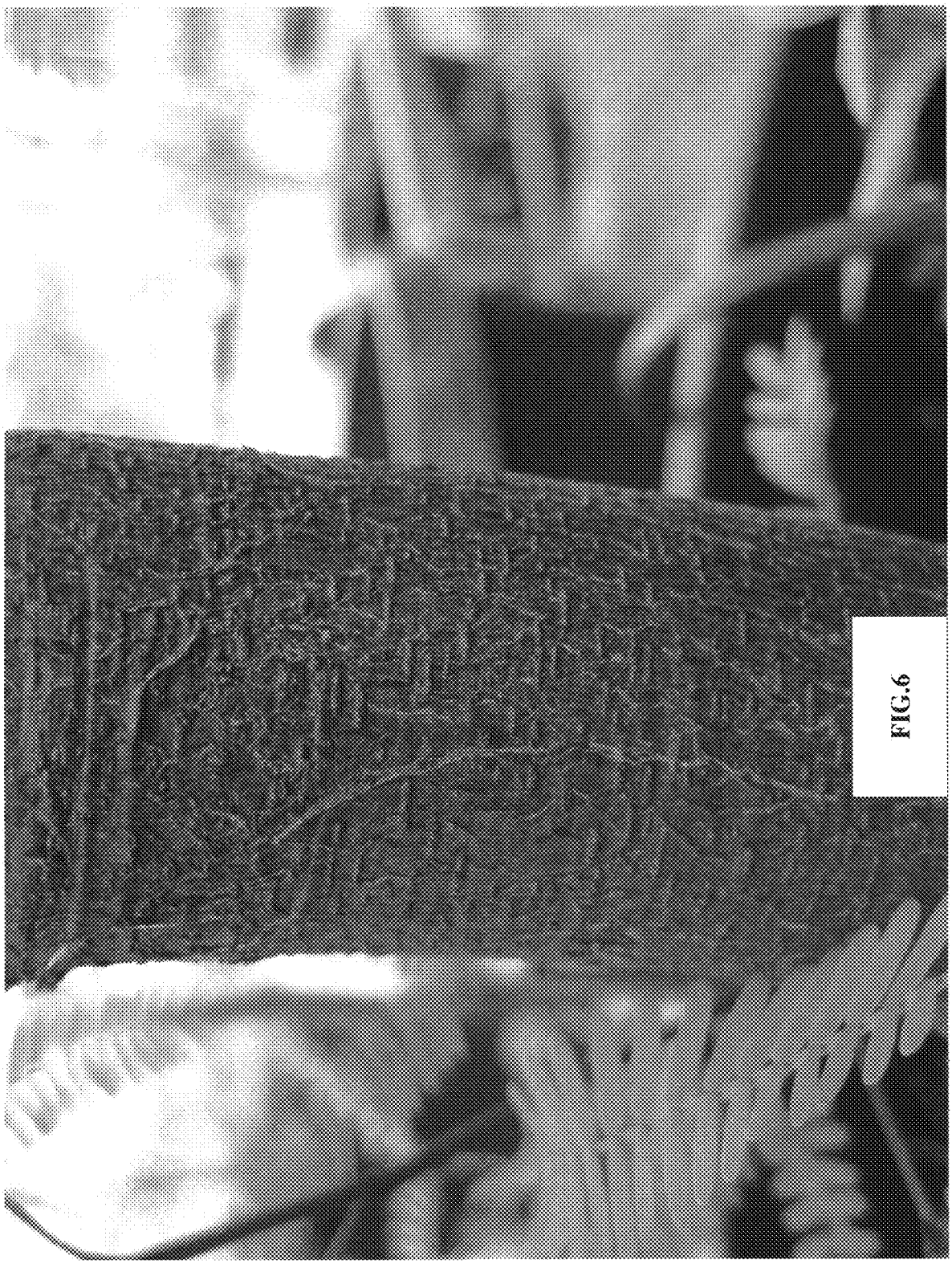
FIG. 6 illustrates the trunk characteristics.

Depending on management, the annual diameter growth ranges from about ½ to ¾ inch per year and the height growth from 3 to 6 ft per year. A 10-year-old tree under good management will be about 6-8 inches in diameter at breast height and 20-25 ft tall. As can be seen in FIG. 6 the color of the trunk is yellow-green group 146A with Greyed-orange group 167A lenticels. The tree has a salinity tolerance to at least 8 dS/m. The clone has a high temperature tolerance of 115° F. and low temperature tolerance of USDA cold hardiness zone 8b. Except for the tropical *P. pallida* which is not deciduous, all other species are deciduous and while 'Mojave' is deciduous, it loses its leaves approximately a month after P. *glandulosa*. 'Mojave' is resistant to the fungal pathogens *Lasiodiplodia, Pestialopsis* and *Phymatotrichum omnivorum.*

The invention claimed is:

1. A new and distinct variety of *Prosopis* named 'Mojave' for use as ornamentals and lumber that combines unique characteristics of North and South American *Prosopis* tree species including cold hardiness to USDA zone 8b, thornlessness, erect growth with branch angles less than 20 degrees and fast growth as described and illustrated herein.

* * * * *